United States Patent [19]
Eckhoff

[11] Patent Number: 5,681,354
[45] Date of Patent: Oct. 28, 1997

[54] ASYMMETRICAL FEMORAL COMPONENT FOR KNEE PROSTHESIS

[75] Inventor: Donald G. Eckhoff, Denver, Colo.

[73] Assignee: Board of Regents, University of Colorado, Boulder, Colo.

[21] Appl. No.: 603,416

[22] Filed: Feb. 20, 1996

[51] Int. Cl.$^6$ ................................................. A61F 2/38
[52] U.S. Cl. .................................... 623/20; 623/18
[58] Field of Search .................................. 623/18, 20

[56] References Cited

U.S. PATENT DOCUMENTS

| | | | |
|---|---|---|---|
| 3,748,662 | 7/1973 | Helfet | 623/20 |
| 3,798,679 | 3/1974 | Ewald | 623/20 |
| 4,714,472 | 12/1987 | Averill et al. | 623/20 |
| 5,133,758 | 7/1992 | Hollister | 623/20 |
| 5,203,807 | 4/1993 | Evans et al. | 623/20 |

OTHER PUBLICATIONS

Anouchi, Y.S., et al. (1993), "The effects of axial rotational alignment of the femoral component on knee stability and patellar tracking in total knee arthroplasty demonstrated on autopsy specimens," Clin. Orthop. 287:170–177.

Arima, J., et al. (1995), "Femoral rotational alignment, based on the anteroposterior axis, in total knee artroplasty in the valgus knee," J. Bone and Joint Surgery 77A:1331–1334.

Bindelglass, D.F., et al. (1993), "Patellar tilt and subluxation in total knee arthroplasty," Clin. Orthop. 286:103–109.

Brattstrom, H. (1964), "Shape of the Intercondylar groove normally and in recurrent dislocation of the patella," Acta Orthop. Scand. 68(Supp):1–24.

Brick, G.W. and Scott, R.D. (1988), "The patellofemoral component of total knee arthroplasty," Clin. Orthop. 231:163–178.

Dye, S.F. (1993, "Patellofemoral Anatomy," In Fox, J.M. and Del Pizzo, W. (eds), The Patellofemoral Joint, New York, McGraw–Hill, 1–12.

Eckhoff, D.G. et al. (1994), "Stereotactic assessment of femoral sulcus location," Orthop. Trans. 18(4):1235–1236.

Eckhoff, D.G. et al., "Assessing Rotational Alignment in Total Knee Arthroplasty," Clinical Orthopaedics (Sep. 1995) 318:176–181.

Fu, F.H., et al. (1993), "Patellofemoral Biomechanics," In Fox, J.M. and Del Pizzo, W. (eds), The Patellofemoral Joint, New York, McGraw–Hill 49–62.

Fulkerson, J.P. and Hungerford, D.S. (1990) "Normal Anatomy, " In Fulkerson, J.P. and Hungerford, D.S. (eds), Disorders of the Patellofemoral Joint, Baltimore, Williams & Wilkins, 1–24.

US Application No. 08/334385 filed Nov. 3, 1994 Considered.

Fulkerson, J.P. and Hungerford, D.S. (1990), "Biomechanics of the Patellofemoral Joint," In Fulkerson, J.P. and Hungerford, D.S. (eds), Disorders of the patellofemoral Joint, Baltimore, Williams & Wilkins, 25–41.

Kapandji (1987), I.A., "The Physiloogy of the Joints," New York, Churchill Livingstone, 76–103.

Walmsley, T. (1933), "The vertical axes of the femur and their relations. A contribution to the study of the erect position," J. Anat. 67:284–300.

Yoshioka, Y., et al. (1987), "The anatomy and functional axes of the femur," J. Bone and Joint Surg. 69A:873–880.

*Primary Examiner*—David Isabella
*Attorney, Agent, or Firm*—Greenlee, Winner and Sullivan, P.C.

[57] ABSTRACT

An asymmetric distal femoral prosthetic component is provided for use in arthroplasty having a sulcus angled laterally upward, and preferably laterally displaced from the midline. This design more closely approximates the configuration of the natural knee and reduces patellar maltracking and excessive wear and failure of the component.

7 Claims, 5 Drawing Sheets

ASYMMETRICAL FEMORAL COMPONENT FOR KNEE PROSTHESIS

FIELD OF THE INVENTION

This invention lies in the field of medical devices, specifically femoral components for artificial knees.

BACKGROUND OF THE INVENTION

Knee replacement has become a common surgical procedure when the natural knee components have either worn out from repeated stress or from advanced disease. A frequent and serious problem in total knee arthroplasty is failure of the implant. This failure is often a result of compression, stress and improper fit of the implant which may not closely approximate the patient's natural knee.

As a commercial consideration, components for knee prostheses are mass-manufactured. It is difficult for the manufacturers to take into account the individual natures of patients' knees. Accordingly, devices now used for total replacement of the anatomical knee joint, in particular the design of the femoral component, have generally tended to be symmetrical in design.

Traditional images of the distal femur place the intercondylar groove (the trochlear groove) midway between the condyles. The location and configuration of the intercondylar groove of the distal femur is clinically significant in the mechanics and pathomechanics of the patellofemoral articulation (Fu, F. H., et al. (1993), "Patellofemoral Biomechanics," In Fox, J. M. and Del Pizzo, W. (eds.), The Patellofemoral Joint, New York, McGraw-Hill 49–62; Fulkerson, J. P. and Hungerford, D. S. (1990), "Biomechanics of the Patellofemoral Joint," In Fulkerson, J. P. and Hungerford, D. S. (eds), Disorders of the Patellofemoral Joint, Baltimore, Williams & Wilkins, 25–41; Kapandji (1987), I. A., The Physiology of the Joints, New York, Churchill Livingstone, 76–103). For this reason, morphologic characteristics of the distal femur have been well documented (Brattstrom, H. (1964), "Shape of the Intercondylar groove normally and in recurrent dislocation of the patella," Acta Orthop. Scand. 68(Supp):1–24; Dye, S. F. (1993, "Patellofemoral Anatomy," In Fox, J. M. and Del Pizzo, W. (eds), The Patellofemoral Joint, New York, McGraw-Hill, 1–2; Fulkerson, J. P. and Hungerford, D. S. (1990) "Normal Anatomy," In Fulkerson, J. P. and Hungerford, D. S. (eds), Disorders of the Patellofemoral Joint, Baltimore, Williams & Wilkins, 1–24; Kapandji (1987), I. A., The Physiology of the Joints, New York, Churchill Livingstone, 76–103; Yoshioka, Y., et al. (1987), "The anatomy and functional axes of the femur," J. Bone and Joint Surg. 69A:873–880.)

Despite numerous investigations devoted to this isolated area of human anatomy, however, no studies have documented the location of the sulcus, the deepest depression of the intercondylar groove, relative to the condyles or its orientation relative to the anatomic and mechanical axes of the femur as defined by Walmsley (Walmsley, T. (1933), "The vertical axes of the femur and their relations. A contribution to the study of the erect position," J. Anat. 67:284–300). The traditional representation of the distal femur with a sulcus lying midway between the femoral condyles cannot be traced to any study where this relationship is supported by anatomic measurement. Yet this traditional image of the femoral sulcus lying midline between femoral condyles has provided the model for prosthetic implants of the knee.

The prosthetic femoral components currently used in total knee replacement are also symmetric with respect to the location of the sulcus between the condyles. That is, contemporary implants locate the distal sulcus in the midline between symmetric condyles. The majority of implants also orient the prosthetic sulcus along the mechanical axis. In some designs such as the Duracon by Howmedica Inc., Rutherford, N.J., the sulcus slopes laterally along the anatomic axis proximally but remains in the midline distally. However, patella tilt, subluxation, and failure documented in total knee arthroplasty (Bindelglass, D. F., et al. (1993, "Patellar tilt and subluxation in total knee arthroplasty," Clin. Orthop. 286:103–109; Brick, G. W. and Scott, R. D. (1988), "The patellofemoral component of total knee arthroplasty," Clin. Orthop. 231:163–179) result from a failure of the patella to track in the non-anatomic sulcus of contemporary femoral prostheses.

Contemporary alignment technique in total knee arthroplasty has been modified to accommodate the symmetry of the femoral component by positioning the component in external rotation. Axial rotation of the femoral component 3 degrees has been documented in a CT scan study to superimpose the patellar groove of the implant over the sulcus of the average patient undergoing total knee arthroplasty as shown by applicant herein. A recent cadaver study reporting 30 distal femoral segments of unknown origin documented that 4 degrees of external rotation of the femoral component relative to the posterior femoral condyles would superimpose the prosthetic and anatomic sulci (Arima, J., et al. (1995), "Femoral rotational alignment, based on the anteroposterior axis, in total knee arthroplasty in the valgus knee," J. Bone and Joint Surgery 77A:1331–1334). External axial rotation of the femoral component five degrees has also been documented in a biomechanical study to improve patellar tracking (Anouchi, Y. S., et al. (1993), "The effects of axial rotational alignment of the femoral component on knee stability and patellar tracking in total knee arthroplasty demonstrated on autopsy specimens," Clin. Orthop. 287:170–177)

The strategy of lateralizing the trochlear groove at the time of implantation by a surgeon externally rotating the component effectively lateralizes the proximal portion of the component but leaves the distal position of the trochlear groove unchanged. The relationship of the femoral component to the tibial component is altered by this method and creates additional wear and failure if the tibial component position is not altered as well. Current efforts of surgeons to deal with a problem created by non-anatomic symmetry of components is producing additional problems and not solving the original problem of patellar maltracking.

A design for improvement of the symmetrical conformation is disclosed in applicant's copending patent application for "Asymmetric Condylar and Trochlear Femoral Knee Component," U.S. Ser. No. 08/334,385 filed Nov. 3, 1994, the disclosure of which is fully incorporated herein by reference. In this design, the sulcus, or low point of the trochlear groove between the condyles, is laterally displaced from the midline of the femoral component to match the knee being replaced, the medial condyle is wider than the lateral condyle, and the lateral condyle is higher than the medial condyle.

Applicant has discovered, and reports herein, that the sulcus axis of the natural knee does not lie in the midline between the femoral condyles, but rather is angled as described below. The patella, which tracks in the sulcus, will naturally track lateral to the midplane of the average femur. This lateral tracking of the patella has been previously documented by others (Anouchi, Y. S., et al. (1993), "The effects of axial rotational alignment of the femoral component on knee stability and patellar tracking in total knee arthroplasty demonstrated on autopsy specimens," Clin. Orthop. 287:170–177), as well as the tendency of the prosthetic patella to tilt and sublux laterally if the sulcus is moved to the midline in the course of a total knee arthroplasty (Bindelglass, D. F., et al. (1993, "Patellar tilt and subluxation in total knee arthroplasty," Clin. Orthop. 286:103–109). Thus, if the natural angle of the sulcus is not preserved in the prosthesis, the patella tends to tip onto one side and ride over to the lateral side, causing excess wear and ultimately failure of the implant.

It is an object of this invention, therefore, to provide a femoral prosthesis for a knee implant approximating the normal knee in design.

There are several femoral components that flair the trochlear groove distally and laterally about 7 degrees from the midline while maintaining the distal sulcus in the midline, including the Zimmer NexGen component and components made by Howmedica and Duracon. This design concept accommodates the patella in knee extension if the femoral component is oriented in neutral rotation; however, these components with "flared" trochlea excessively lateralize the anterior sulcus relative to its natural location if the component is externally rotated, introducing the potential for patellar tilt and subluxation in a medial direction when the knee is extended.

SUMMARY OF THE INVENTION

An asymmetric distal femoral component for a knee prosthesis is provided having a sulcus on its frontal and distal sides, wherein the medial angle between the sulcus and the joint line is between about 90 and 97 degrees on the front side (as shown in FIG. 1). More preferably, said angle between the sulcus and the joint line is between about 93 and about 95 degrees.

The joint line is the line defined by the lowest points of the condyles when the joint is placed with the distal side contacting a horizontal surface. The same definition is used for the joint line of the prosthetic component. As will be understood by those skilled in the art, the angles are measured on a two-dimensional projection of the image of the front of the distal femur, or the front of the prosthetic component.

The sulcus of the natural knee, which is the lowest point of the trochlear groove, runs in a substantially straight line from the front of the femur through the point defined as the origin of the sulcus herein which is the highest (closest to the patella) point of the sulcus visible in a distal view of the femur. The origin of the sulcus is laterally displaced from the midline in the natural knee, and preferably also in the asymmetric femoral component of this invention. Preferably, the sulcus origin of the asymmetric component is displaced laterally from the midline a distance of between about 1 and about 15 mm, more preferably between about 3 and about 8 mm, and most preferably a distance of about 5 mm.

It is preferred that the asymmetric component of this invention have a medial condyle which is wider than its lateral condyle by about 3 mm to about 8 mm, and preferably about 5 mm.

It is also preferred that the asymmetric component of this invention have a lateral condyle which is higher than its medial condyle by about 1 mm to about 5 mm, and preferably about 3 mm.

As will be appreciated by those skilled in the art, the component for the patient's right knee will be a mirror image of the component for the patient's left knee.

DETAILED DESCRIPTION OF THE PREFERRED EMBODIMENTS

Figure 4:
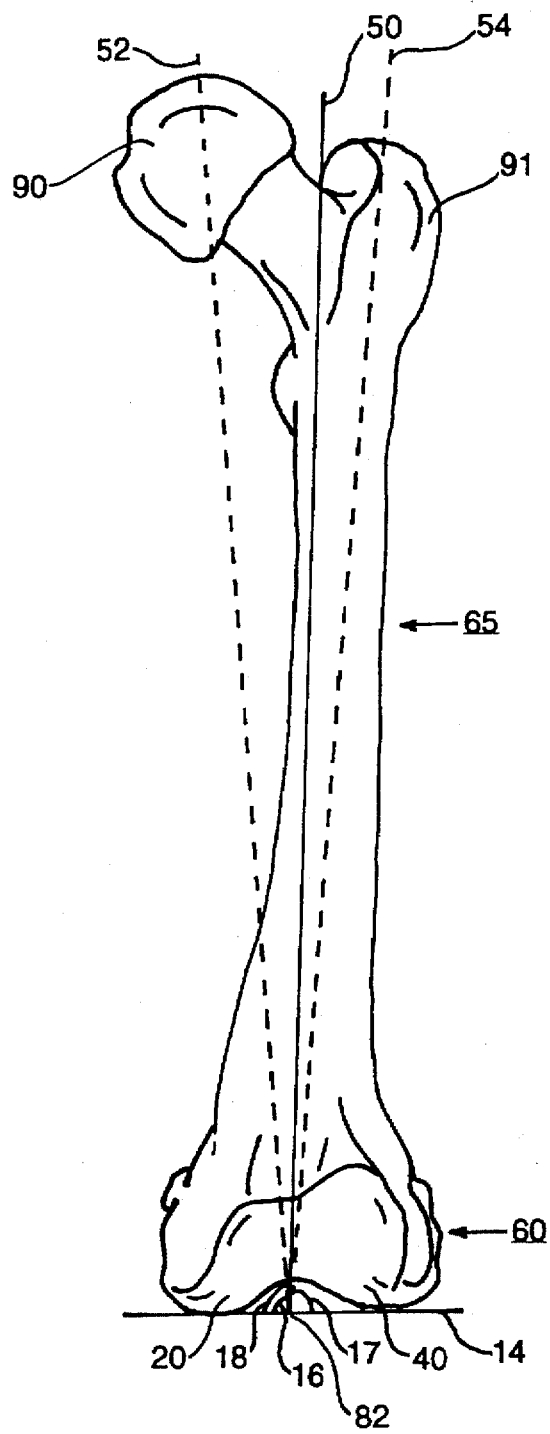
FIG. 4 shows the axis of the sulcus lying between the mechanical and anatomic axes of the average femur.

Applicants have discovered that in the natural distal femur, the sulcus is linear, and the origin of the sulcus is lateral to the midplane. The natural sulcus has been found to be about 94.7 degrees plus or minus 0.9 degrees from the joint line when viewed frontally (FIG. 4). This contrasts with the traditional symmetrical image of the distal femur (FIG. 2) presented in anatomic and orthopaedic literature.

A femoral component for an implant for total knee replacement is provided by this invention which comprises a sulcus angled laterally from the joint line (as viewed from the front) to more closely approximate the conformation of the natural knee. This allows more natural patellar tracking in the component and reduces excess wear and premature failure of the implant.

Figure 2:
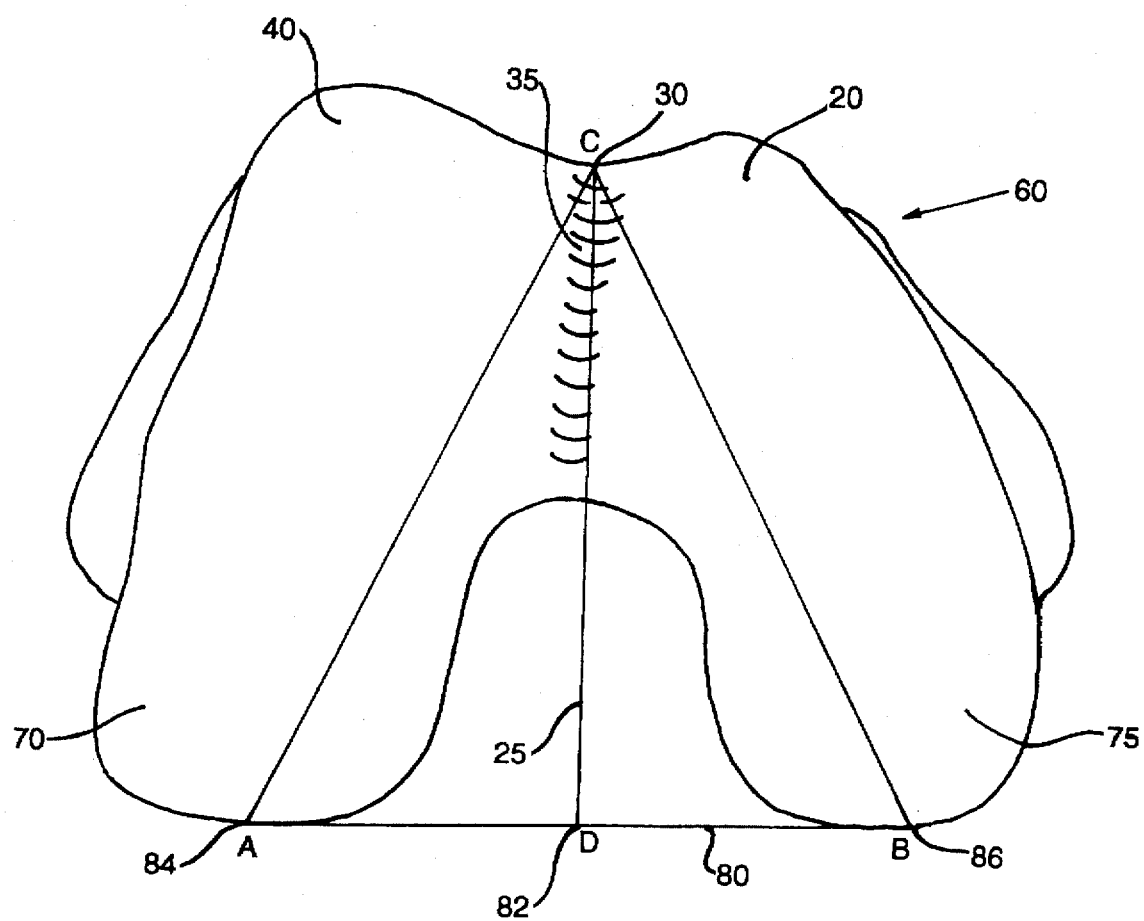
FIG. 2 shows a traditional image of a distal femur demonstrating the symmetric placement of the sulcus relative to the femoral condyles.

FIG. 2 shows a traditional image of a distal femur 60, upon which most currently used femoral component designs are modelled. The distal femur 60 comprises a medial condyle 20 and a lateral condyle 40 with a trochlear groove 35 between them. The lowest point of the trochlear groove 35 is called the sulcus, and its endpoint at the top of FIG. 2 is termed the sulcus origin 30 herein, which also corresponds to point C on FIG. 2. The distal femur 60 also comprises a lateral posterior femoral condyle 70 having a lowest point 84 (shown as center point A) and a medial posterior femoral condyle 75 having a lowest point 86 (shown as center point B). The lowest points 84 and 86 are connected by notional baseline 80. The notional triangle created by connecting the center points of the two posterior femoral condyles, A and B, with the sulcus origin, C, is isosceles with distance A–C equal to B–C. The symmetry of the traditional image is further demonstrated by the intersection 82 of the baseline 80 (line A–B) with its perpendicular bisector, distal femoral midline 25 (line C–D).

Figure 1:
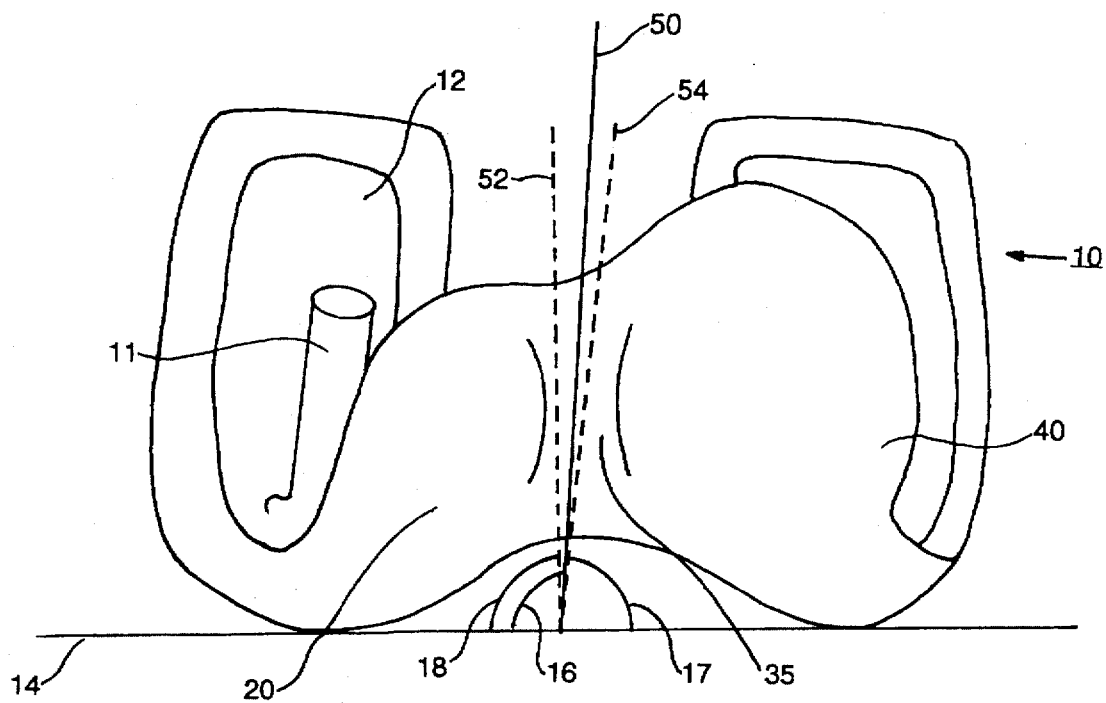
FIG. 1 shows a frontal view of an asymmetric distal femoral prosthetic component of this invention for a left knee having a sulcus axis 50 at a 93 degree angle from the joint line 14.

FIG. 1 shows an asymmetric femoral prosthetic component 10 of this invention having posterior flanges 12, pins 11, a medial condyle 20 and a lateral condyle 40 separated by a trochlear groove 35. The line defined by the condyles where they rest on a horizontal surface is joint line 14. In the natural knee, as shown in FIG. 4, the mechanical axis 52, a notional line joining the head of the femur to the midpoint between the condyles, lies at a 90 degree angle to the joint line. The anatomic axis 54 (a notional line joining the center of the proximal shaft of the femur to the midpoint between the condyles, is typically about 7 degrees lateral to the mechanical axis 52. The typical sulcus axis 50 lies between the mechanical axis 52 and the anatomic axis 54. In the asymmetric femoral prosthetic component 10 of this invention, the sulcus axis 50 is similarly placed. Thus the medial sulcus-joint line angle 16 is preferably about 93 degrees (the angle is measured from the medial side). The mechanical axis-joint line angle 18 is about 90 degrees as discussed above. The lateral anatomic axis-joint line angle 17 is preferably about 83 degrees (the angle is measured from the lateral side).

Figure 3:
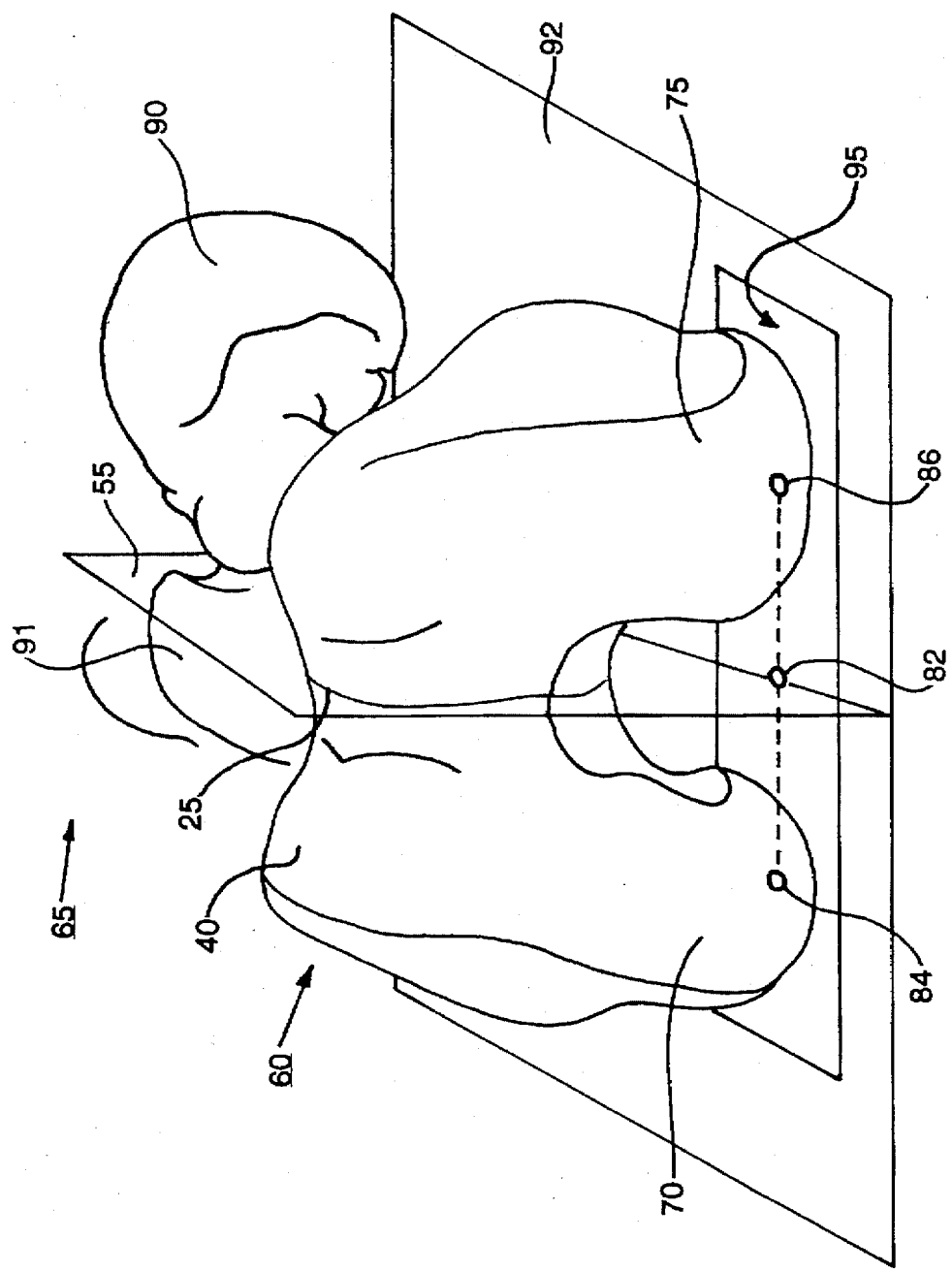
FIG. 3 shows a distal femur depicting how the midpoint was determined by measuring one-half the distance between the contact points of the femoral condyles with the base of a stereotactic device (contact plane).

FIG. 3 shows a femur 65 with the distal femur 60 in the foreground and the head 90 and greater trochanter 91 in the background at the proximal end. The femur rests on a horizontal surface or contact plane 92 with the head 90 and lateral posterior femoral condyle 70 and medial posterior femoral condyle 75 resting on the contact plane 92. The medial posterior femoral condyle lowest point 86 and the lateral posterior femoral condyle lowest point 84 rest on contact points on pressure sensitive paper 95. Midpoint 82 was determined by measuring one-half the distance between lowest points 84 and 86 with the base of a stereotactic device (not shown) lying in the contact plane 92. Midplane 55 is perpendicular to contact plane 92 at midpoint 82, i.e. midplane 55 is perpendicular to the line joining medial posterior femoral condyle lowest point 86 and lateral posterior femoral condyle lowest point 86 (shown as baseline 80 on FIG. 2).

FIG. 4 shows a femur 65 having a distal femur 60 with a head 90, a greater trochanter 91, a medial condyle 20, and a lateral condyle 40. Also depicted in FIG. 4 is the anatomic axis 54 (dotted line) which is defined as a notional line joining the center of the proximal shaft of the femur to the midpoint 82, and the mechanical axis 52 (dotted line) which is defined as a notional line joining the center of the head 90 to the midpoint 82. The sulcus axis 50 of the average femur corresponds with the actual sulcus, and lies at an angle from the mechanical axis 52 and the mechanical axis 54.

Figure 5:
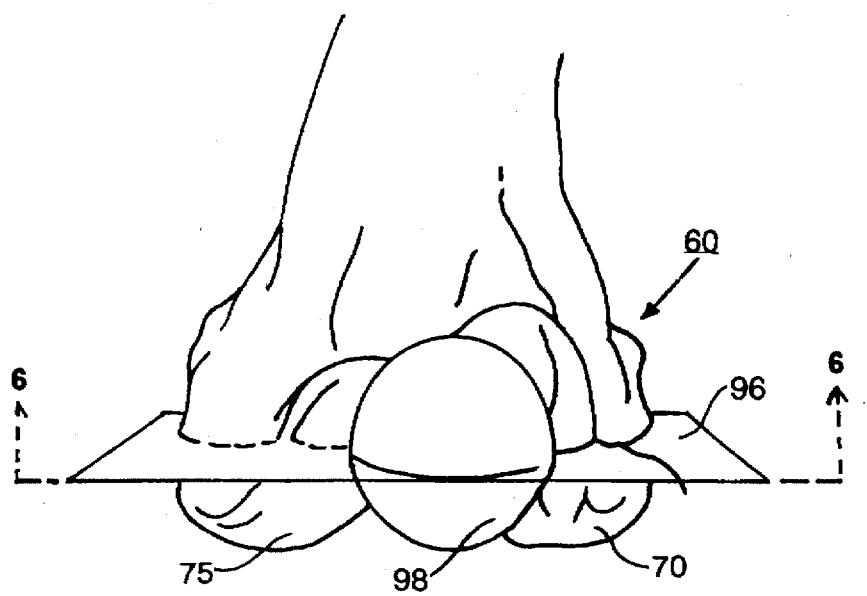
FIG. 5 illustrates the distal femur with computed tomography scan with cut one cm above the intercondylar notch.

FIG. 5 shows the distal femur 60 with the plane of a computed tomography (CT) scan 96 shown where a single cut was taken through the distal femur 60 proximal to the intercondylar notch (shown obscured by the patella 98).

Figure 6:
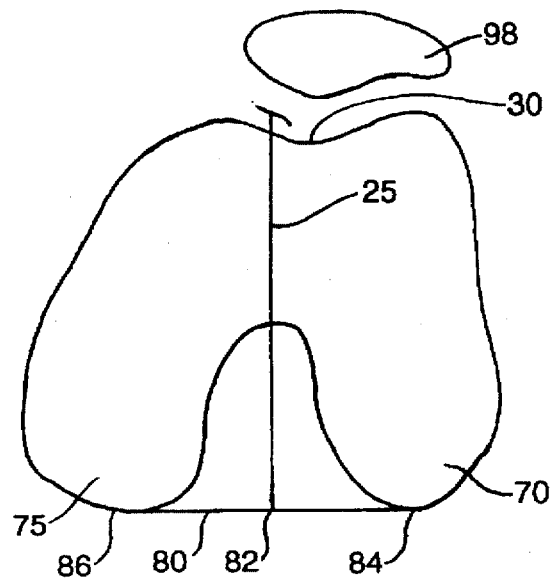
FIG. 6 is a cross-section along line 6—6 of FIG. 5 illustrating the baseline, midline and sulcus origin with lateral displacement of the sulcus.

FIG. 6 shows the plane of the scan along line 6—6 of FIG. 5 with the sulcus origin 30 displaced from the midline 25. The midline 25 is constructed by constructing a baseline 80 between the medial posterior femoral condyle lowest point 86 and the lateral posterior femoral condyle lowest point 84, determining the midpoint 82 and constructing a perpendicular identified as the midline 25.

In the preferred asymmetric distal femoral prosthetic component of this invention, the sulcus axis is inclined between about 1 and about 3 degrees, and preferably about 2 degrees from the anatomic axis and between about 3 and about 5 degrees, and preferably about 4 degrees from the mechanical axis (the latter axes being defined when the component is in place in the patient's knee).

The origin of the sulcus is also preferably displaced laterally from the midline as described above, the medial condyle is wider than the lateral condyle, and the lateral condyle is higher than the medial condyle.

The asymmetric component of this invention is used in standard arthroplasty procedures as known to the art. Preferably a selection of asymmetric components are available to the physician with varying sulcus angles, and a component is selected which most closely approximates the sulcus angle observed in the patient's natural knee. Such observations can be made by CT scan of the distal femur as described in Example 1, wherein the angle of the sulcus relative to the midline is measured e.g. by using a plastic overlay to mark the baseline, midline, and sulcus origin. First and second CT scans of the distal femur taken at parallel cuts as far apart as possible can be superimposed, and the sulcus termination, sulcus axis, and sulcus angle determined from the computer images, so that the correct sulcus angle for the prosthesis to match the naturally occurring angle may be chosen.

EXAMPLE 1

The specific focus of this study was to measure the horizontal, that is, mediolateral, position of the sulcus relative to the condyles. Forty osteoarthritic knees (20 left, 20 right) in patients presenting for total knee arthroplasty (TKA) and 20 control knees in 10 asymptomatic adults were randomly selected for study. The osteoarthritic patients all met the clinical and radiographic criteria for advanced osteoarthritis requisite for TKA. The control subjects were screened by history, physical examination, and radiographs to exclude anyone with signs or symptoms suggesting occult arthritis of the knee. No patient or volunteer demonstrated evidence of traumatic deformity.

Patient and control computed tomography (CT) scans were obtained with the individual supine, the knees in full extension, and the feet and toes together. A single cut was taken through the distal femur proximal to the intercondylar notch (FIG. 5). The scanning was limited to a single cut (FIG. 6) to avoid excessive cost and radiation exposure. The single cut was further justified on the basis of preliminary studies of 79 cadaver femurs using a stereotactic device that demonstrated no statistically significant mediolateral deviation of the sulcus relative to the two contact points when the lowest point in the trochlea (sulcus) was measured at 3-mm increments throughout the length of the femoral trochlea (Eckhoff, D. G., et al. (1994), "Stereotactic assessment of femoral sulcus location," Orthop. Trans. 184:1235).

The most posterior point on the articular surface of each femoral condyle was identified on the CT image and the line connecting these two points was constructed (FIG. 6). The perpendicular bisector of this baseline was drawn to intersect with the trochlea. This perpendicular bisector of the baseline was designated the midline. The lowest point of the trochlea, designated the sulcus, was determined and the magnitude and direction of displacement of the sulcus from the midline were measured as the sulcus displacement. This measurement of sulcus displacement was performed on the screen of the CT console and on the CT films (hard copy) after calibrating the degree of magnification with a CT phantom (1 CT pixel=1 mm on specimen).

The translation of the sulcus from the midline in patients requiring TKA was 5 plus or minus 1 mm in a lateral direction. The translation of the sulcus from the midline in asymptomatic volunteers was 4 plus or minus 1 mm in a lateral direction. The data were analyzed using an unpaired t-test and there was no significant difference between patients and control subjects (P>0.05). There was no significant difference between right and left in patients or control subjects (P>0.05). There was no intraobserver or interobserver significant difference tested by analysis of variance when two independent observers each repeated the measurements twice.

From the standpoint of artistic rendering, the 4- to 5-mm displacement of the sulcus identified in this study may be an insignificant amount, the omission of which falls within the artistic license of an illustrator. The significance of these data is in their engineering application to TKA. The lateralized sulcus describes not only the shape of the distal femur but it also reflects the location occupied by the patella prior to surgical intervention. Like the traditional image, most femoral components in contemporary TKA are symmetric and place the sulcus in the midline relative to the posterior femoral condyles. These components force the patella into the midline even though it tracked lateral to the midline before surgery. This observation may account of the high incidence of postoperative patellar tilt and subluxation in TKA.

EXAMPLE 2

The purpose of this study was to measure the location of the sulcus of the distal femur in a large series of cadaver femora using a custom stereotactic device. This study was designed to document the position of the sulcus relative to the posterior femoral condyles and the orientation of the sulcus relative to the traditional axes of the femur.

Eighty-five right femora located in the Anthropology Department of the University of Colorado were measured in this study. All femora were well preserved by virtue of the fact that they were buried in an arid region of Sudanese Nubia and each corpse became naturally mummified by desiccation in the dry soil. Femora from 38 females and 47 males were studied. All femora were skeletally mature with chronological ages between 21 and 51 years of age (average forty years). Age and gender were determined by an experienced anthropologist (DPV) using accepted anthropologic techniques that require staging the development of the symphysis pubis and careful measure of the inlet and outlet dimensions (Ubelaker, D. H. (1978), Human Skeletal Remains—Excavation, Analysis, Interpretation, New York, Aldine-Hawthorne 42–43, 53–55). Femora were not studied if gender and age could not be determined. Femora that were poorly preserved, traumatically deformesufficient degree arthritic disease of sufficient degree to compromise accurate measurement of the femoral sulcus and condyles were not included in the study.

All femora were measured in the following fashion: A stereotactic device used for localizing lesions of the brain in animal neurosurgery was modified to hold a femur at an inclination of 45 degrees to the horizontal. The forty-five degree inclination provided the optimal orientation of the femur with respect to the stylus of the device to allow measurement from top to bottom of the trochlea without repositioning the specimen during the measuring procedure. The condyles were held 8 mm from the side wall of the device by a shim while the femoral head rested against the side wall. This position was found empirically to facilitate measurement of the axes and had no effect on the relative values measured since this position was maintained for all measurements of all bones.

The location and orientation of the sulcus were obtained by repeated horizontal passes of the stereotactic stylus over the distal femur beginning at the top of the articular surface and progressing down to the intercondylar notch. With each horizontal pass, the lowest depression of the trochlea (sulcus) was identified by the stereotactic stylus and the coordinates were recorded. After each horizontal pass, the stereotactic device was lowered by 2 mm to provide sequential horizontal tracings.

The sulcus data were analyzed by establishing the following references. The floor of the device defined the contact plane of the femoral condyles and greater trochanter (FIG. 3). The posterior femoral condyle contact points were identified by the imprint of the condyles on pressure-sensitive contact paper (Fuji Film, Fuji Photo Film Co., Ltd., Tokyo, Japan), located on the floor of the device (FIG. 3). The midpoint between the two contact points was identified by direct measure of the contact paper with a ruler fixed to the floor of the device. The location of the sulcus was measured in reference to an imaginary midplane, erected as the perpendicular plane to the contact plane (floor of the device) at the midpoint (FIG. 3). The midplane represented the null point from which the displacement of the sulcus in a medial or lateral direction was measured in millimeters by the stylus and micrometer.

The anatomic axis, defined by the line joining the center of the proximal shaft to the midpoint of the condyles, and the mechanical axis, defined by the line joining the center of the head to the midpoint of the condyles, were measured relative to the midplane. The inclination of the sulcus, the sulcus axis, was determined by plotting the sulcus data on metric graph paper. A straight line representing the axis of the sulcus was produced by placing a straight edge through the data points. The inclination of this sulcus axis relative to the projection of the midplane on the graph paper was determined. The anatomic and mechanical axes of each femur were superimposed on the sulcus plots and the deviation in degrees between the sulcus axis and the traditional femoral axes (anatomic and mechanical) were measured (FIG. 4).

Three repeated measures performed by each of three independent observers were compared b one-way analysis of variance to demonstrate repeatability and reliability of the stereotactic measurement method.

The lateral displacement of the sulcus axis from the midplane measured 2.4 plus or minus 2.1 mm (range, −2.5±8.3 mm) for the 85 femora. There was virtually no medial or lateral deviation of the sulcus with respect to the sulcus axis. The maximum displacement of any data point from the axis was less than plus or minus 0.5 mm for any sulcus, showing that the femoral sulcus is a linear structure and this method is accurate within the limits of measure in defining its orientation.

The angle of inclination of the sulcus axis relative to the midplane was 0.4 degrees plus or minus 5 degrees. The difference between the sulcus axis and the anatomic axis of the femur was 1.7 degrees plus or minus 0.9 degrees. The difference between the sulcus axis and the mechanical axis of the femur was 3.6 degrees plus or minus 0.5 degrees.

The difference in average sulcus displacement reported following repeated measures by a single independent observer was <1 mm. The difference between the three independent observers in reported sulcus displacement averaged <1 mm. There was no significant difference between observers or between repeated measures of a single observer demonstrated by analysis of variance. These internal reliability checks demonstrate the method and the apparatus are both accurate and reproducible.

This study documents that the configuration of the femoral sulcus is linear with little medial-lateral deviation. The data further illustrate that the average femoral sulcus is lateral to the midplane and the majority of femoral sulci lie between 0 and 5 mm of the midplane. The orientation of the average sulcus lies between the traditional anatomic and mechanical axes of the femur, but this orientation demonstrates variability with some sulci lying medial to the mechanical axis and others lying lateral to the anatomic axis.

These observations reflect the characteristics of a unique skeletal population and should not be interpreted as a characterization of all femoral sulci. These femora belonged to a Black population and it is well established that the femur is longer and narrower in Black as compared to White populations. The sulcus should be more lateral in the wider femur of a White population and an average of 5 mm lateralization has been documented in a study using CT scans on Caucasian patients undergoing total knee arthroplasty (Example 1). Interpretation of the data in this study is further limited by the fact that measurements were performed only on right femora as the left femora in this population were unavailable. However, a prior study demonstrated no significant difference in sulcus location between right and left femora (Example 1).

I claim:

1. An asymmetric distal femoral component for a knee prosthesis having frontal and distal sides, said component comprising a medial condyle and a lateral condyle defining a notional joint line, and a notional midline, said component further comprising a sulcus on said frontal and distal sides between said condyles, said sulcus having a medial angle with said joint line between about 90 and 97 degrees on said front side, and having a sulcus origin displaced from said midline, wherein said medial condyle is wider than said lateral condyle and said lateral condyle is higher than said medial condyle.

2. The asymmetric component of claim 1 wherein the medial angle between the sulcus and the joint line is between about 93 and about 95 degrees on the front side.

3. The asymmetric component of claim 1 for a patient's right knee wherein said wider medial component is on said component's left side.

4. The asymmetric component of claim 1 for a patient's left knee wherein said wider medial component is on said component's right side.

5. The asymmetric component of claim 1 wherein the sulcus origin is displaced laterally from the midline.

6. The asymmetric component of claim 5 wherein said sulcus origin is displaced from said midline about 3 to about 8 mm.

7. The asymmetric component of claim 5 wherein the displacement of the sulcus origin from the midline is about 5 mm.

* * * * *

UNITED STATES PATENT AND TRADEMARK OFFICE
CERTIFICATE OF CORRECTION

PATENT NO.    : 5,681,354

DATED         : October 28, 1997

INVENTOR(S)   : Donald G. Eckhoff

It is certified that error appears in the above-identified patent and that said Letters Patent is hereby corrected as shown below:

In column 7, line 41, delete "deformesufficient degree" and replace with --deformed, or demonstrated--.

Signed and Sealed this

Thirteenth Day of January, 1998

Attest:

BRUCE LEHMAN

Attesting Officer        Commissioner of Patents and Trademarks